(12) United States Patent
Jendrisak et al.

(10) Patent No.: US 6,190,865 B1
(45) Date of Patent: *Feb. 20, 2001

(54) METHOD FOR CHARACTERIZING NUCLEIC ACID MOLECULES

(75) Inventors: Jerome J. Jendrisak; Leslie M. Hoffman; Robert E. Smith, all of Madison, WI (US)

(73) Assignee: Epicentre Technologies Corporation, Madison, WI (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/534,799

(22) Filed: Sep. 27, 1995

(51) Int. Cl.$^7$ .............................. C12Q 1/68; C12P 19/34
(52) U.S. Cl. ............................................. 435/6; 435/91.2
(58) Field of Search ................... 435/6, 91.2; 935/77.78

(56) References Cited

U.S. PATENT DOCUMENTS 5,035,996  7/1991  Hartley ..................................... 435/6

FOREIGN PATENT DOCUMENTS

| 0 684 315 A1 | 3/1995 | (EP) . |
| WO 95/06752 | 3/1995 | (WO) . |
| WO/97/03210 | 1/1997 | (WO) . |

OTHER PUBLICATIONS

P. R. Devchand, et al., "Uracil–DNA glycosylase as a probe for protein–DNA interactions," *Nucl. Acids Res.* 21 (15) :3437–3443, 1993.

Saparbaev et al, PNAS 91: 5873–5877 (1994).*

Dianov et al, Nucleic Acid Res 19:3829–3833 (1991).*

W.T. Pu and K. Struhl, "Uracil interference, a rapid and general method for defining protein–DNA interactions involving the 5–methyl group of thymines: The GCN4–DNA complex, " *Nucl. Acids Res.* 20 (4) :771–775, 1992.

Bessmans, et al., "Enzymatic Synthesis of Deoxyribonucleic Acid. III. The Incorporation of Pyrimidine and Purine Analogues into Deoxyribonucleic Acid," *Proc. Natl. Acad. Sci. USA* 44 (7):663–640, 1958.

Cannon, et al., "5–hydroxymethylcytosine DNA Glycosylase Activity in Mammalian Tissue," *Biochem. Biophys. Res. Commun.* 151(3):1173–1179, 1988.

Cook, et al., "Enzyme–labelled Oligonucleotides for the Detection of $\alpha_1$–antitrypsin Deficiency: Optimization of Enzyme Activity for Single Point Mutation Detection, " *Ann. Clin. Biochem.* 32:91–93, 1995.

Cotton, "Current Methods of Mutation Detection, " *Mutation Research* 285:125–144, 1993.

Cox, "$\alpha_1$–antitrypsin Deficiency," in *The Metabolic Basis of Inherited Disease*, 6th Ed., Scriver, et al., eds., McGraw–Hill, New York, NY, p. 2409–2437, 1990.

Demple and Harrison, "Repair of Oxidative Damage to DNA," *Annu. Rev. Biochem.* 63:915–48, 1994.

Duncan, "DNA Glycosylases," in *The Enzymes*, Boyer ed., p. 565–586, 1981.

Fahy, et al., "Self–sustained Sequence Replication (3SR): An Isothermal Transcription–based Amplification System Alternative to PCR," *PCR Meth. Applic.* 1:25–33, 1991.

Karran and Lindahl, "Enzymatic Excision of Free Hypoxanthine from Polydeoxynucleotides and DNA Containing Deoxyinosine Monophosphate Residues," *J. Biol. Chem.* 253(17):5877–5879, 1978.

Karran and Lindahl, "Hypoxanthine in Deoxyribonucleic Acid: Generation by Heat–Induced Hydrolysis of Adenine Residues and Release in Free Form by a Deoxyribonucleic Acid Glycosylase from Calf Thymus, " *Biochemistry* 19:6005–6011, 1980.

Kwoh, et al., "Transcription–based amplification system and Detection of Amplified Human Immunodeficiency Virus Type 1 with a Bead–based Sandwich Hydridization Format," *Proc. Natl. Acad. Sci. USA* 86:1173–1177, 1989.

Lindahl, "An N–Glycosidase from *Escherichia coli* that Releases Free Uracil from DNA Containing Deaminated Cytosine Residues," *Proc. Natl. Acad. Sci. USA* 71(9):3649–3653, 1974.

Lindahl, "DNA Glycosylases, Endonucleases for Apurinic/Apyrimidinic Sites, and Base Excision–Repair," *Prog. Nucl. Acid Res. Mol. Biol.* 22:135–192, 1979.

Maxam and Gilbert, "A New Method for Sequencing DNA," *Proc. Natl. Acad. Sci. USA* 74(2):560–564, 1977.

Merajver, et al., "Somatic Mutations in the *BRCA1* Gene in Sporadic Ovarian Tumours," *Nature Genetics* 9:439–443, 1995.

Myers and Gelfand, "Reverse Transcription and DNA Amplification by a *Thermus thermophilus* DNA Polymerase," *Biochemistry* 30(31):7661–7666, 1991.

(List continued on next page.)

*Primary Examiner*—Eggerton A. Campbell
(74) *Attorney, Agent, or Firm*—Quarles & Brady LLP

(57) ABSTRACT

A method of characterizing a nucleic acid molecule is disclosed. The method comprises synthesizing DNA in the presence of a reaction mixture comprising a nucleic acid template, a primer molecule, an enzyme that extends the primer so that a DNA molecule may be synthesized, four canonical deoxynucleoside triphosphates and at least one non-canonical deoxynucleoside triphosphate. The non-canonical deoxynucleoside triphosphate is incorporated into the synthesized DNA in place of a portion of only one canonical deoxynucleoside triphosphate. The synthesized DNA is treated with an N-glycosylase that excises a base portion of the non-canonical deoxynucleoside triphosphate from the synthesized DNA. The DNA is then treated in such a manner that the phosphodiester backbone of the DNA is broken at the abasic site, thus creating at least two DNA fragments. The fragments are separated according to size.

25 Claims, 5 Drawing Sheets

OTHER PUBLICATIONS

Nisson, et al., "Rapid and Efficient Cloning of Alu–PCR Products Using Uracil DNA Glycosylase," *PCR Meth. Applic.* 1:120–123, 1991.

Sanger, et al., "DNA Sequencing with Chain–terminating Inhibitors," *Proc. Natl. Acad. Sci. USA* 74(12):5463–5467, 1977.

Stahl and Chamberlin, "Groups on the Outside of the DNA Helix Affect Promoter Utilization by T7 RNA Polymerase", in *RIVA Polymerase* Losich and Chamberlin eds., Cold Spring Harbor Press, Cold Spring Harbor, NY, p. 429–440, 1976.

Yap and McGee, "Detection of Mutations by PCR, " in PCR Technology, Griffin and Griffin, eds., CRC Press, Boca Raton, FL, p. 107–120, 1994.

* cited by examiner

```
                            SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (oglionucleotide)

(xi) SEQUENCE DESCRIPTION: SEQ ID NO:1:

GAGGAGGAGC AAGGCCTATG TG                                              22

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (oglionucleotide)

(xi) SEQUENCE DESCRIPTION: SEQ ID NO:2:

GGGATTCACC ACTTTTCCCA TG                                              22

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:3:

AGGGATCCCC GCAGAGGATT TCGTGTACC                                       29

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:4:

GAGCTGCAGG TAGTTGTGTC TGCACAC                                         27

(2) INFORMATION FOR SEQ ID NO:5:

(i) SEQUENCE CHARACTERISTICS:
        (A) LENGTH: 24 base pairs
        (B) TYPE: nucleic acid
```

```
            (C) STRANDEDNESS: single
            (D) TOPOLOGY: linear (ii) MOLECULE TYPE: DNA (oligonucleotide)

(xi) SEQUENCE DESCRIPTION: SEQ ID NO:5:

CGCCAGGGTT TTCCCAGTCA CGAC                                              24

(2) INFORMATION FOR SEQ ID NO:6:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO:6:

AGCGGATAAC AATTTCACAC AGGA                                              24
```

METHOD FOR CHARACTERIZING NUCLEIC ACID MOLECULES

FIELD OF THE INVENTION

The field of the present invention is methods of characterizing nucleic acid molecules. Specifically, the present invention concerns characterizing nucleic acid molecules by synthesizing DNA in the presence of a non-canonical deoxynucleoside triphosphate, excising the base portion of the non-canonical deoxynucleoside triphosphate, breaking the phosphodiester backbone of the DNA at the abasic sites, and analyzing the resulting DNA fragments.

BACKGROUND OF THE INVENTION

Methods of Characterizing Nucleic Acid Molecules

There are many reasons for characterizing nucleic acid molecules. For example, genes are rapidly being identified and characterized which are causative or related to many human, animal and plant diseases. Even within any particular gene, numerous mutations are being identified that are responsible for particular pathological conditions. Thus, although many methods for detection of both known and unknown mutations have been developed (e.g., see Cotton, 1993), our growing knowledge of human and other genomes makes it increasingly important to develop new, better, and faster methods for characterizing nucleic acids. Besides diagnostic uses, improved methods for rapidly characterizing nucleic acids will also be useful in many other areas, including human forensics, paternity testing, animal and plant breeding, tissue typing, screening for smuggling of endangered species, and biological research.

A variety of methods for characterizing DNA molecules are known in the art. For example, one can characterize DNA molecules by size based on their electrophoretic migration through an agarose or polyacrylamide gel. In these methods, the negatively charged DNA molecules move through a gel in the direction of the positively charged electrode. Provided that the percentage of agarose or polyacrylamide in the gel is appropriate for the size range of the DNA molecules being electrophoresed, smaller DNA molecules move through the pores of the gel more readily than larger DNA molecules. Because DNA molecules move in the gel at size-dependent rates, molecule sizes can be determined by staining and visualizing the DNA and then comparing the migration of the sample DNA molecules in the gel with the migration of marker DNA molecules of known size. Under the appropriate conditions, single-stranded DNA molecules differing in length by even a single nucleotide can be distinguished by denaturing polyacrylamide gel electrophoresis.

Another way to characterize DNA molecules is to treat each DNA molecule with one or more restriction endonucleases and then to determine the sizes of the various DNA fragments resulting from this treatment by agarose gel electrophoresis. Restriction endonucleases are enzymes that recognize specific sequences of bases in DNA (often 4, 5, 6 or sometimes 8 bases on each DNA strand) and then cut the phosphodiester bonds of the polynucleotide chains of DNA within to the recognition sequence. Because many restriction endonucleases with different recognition sequences are available, one can obtain a restriction map of an entire DNA molecule showing locations of restriction enzyme recognition sites and distances between them by determining which other restriction enzymes will cut each DNA fragment generated by any given restriction enzyme and what are the sizes of all of the resulting fragments. Such a restriction map is characteristic for a particular DNA molecule and can be used to obtain a rough identification of a particular sequence. Additionally, changes such as those caused by mutations in DNA may result in a loss or gain of a restriction site—a so-called "restriction fragment length polymorphism" (RFLP) (Kazazian, et al., 1989). An example of a diagnostically significant RFLP is a single base mutation in the beta-hemoglobin gene, the change from A to T which eliminates a Dde I restriction site, which results in sickle cell anemia (Kazazian, et al., 1989).

One of the most informative ways to characterize a DNA molecule is to determine its nucleotide sequence. One method for sequencing DNA (Maxam and Gilbert, 1977) is accomplished by treating each of four aliquots of one strand of a 5'- or 3'-end-labelled DNA molecule to be sequenced with one of four different chemical reagents. One chemical specifically modifies only the guanine base in the DNA, another modifies only cytosine, another modifies either guanine or adenine bases, and the last chemical modifies either thymine or cytosine bases. The chemical treatments are carried out under conditions so that only a small proportion of the total susceptible bases will actually be modified.

It is important that the chemical reactions are limited in order to generate a nested set of fragments differing by one base of a specific type. If all G residues, for example, were modified, the residues would all be susceptible to phosphodiester bond cleavage. Therefore, a collection of partially modified nucleic acids is required for sequencing. Subsequent treatment with piperidine results in cleavage of the phosphodiester bonds of the DNA molecule at the abasic sites, generating a mixture of all sizes of DNA molecules that are possible following chemical modification and loss of each one of the corresponding susceptible bases. The DNA molecules in each of the four reactions are then resolved by electrophoresis in adjacent lanes of a polyacrylamide gel and the pattern of bands is revealed by exposing the gel to X-ray film if the DNA molecules are labelled with a radioisotope. The sequence of the DNA is revealed by analyzing the exposed X-ray film. Alternatively, if the DNA molecules are labelled with a fluorescent, chemiluminescent or some other non-radioactive moiety, the sequence is revealed by an appropriate method known in the art.

The most commonly used method for sequencing DNA at this time (Sanger, et al., 1977) uses a DNA polymerase to produce differently sized fragments depending on the positions (sequence) of the four canonical bases (A=Adenine; C=Cytidine; G=Guanine; and T=Thymine) within the DNA to be sequenced. In this method, the DNA to be sequenced is used as a template for in vitro DNA synthesis. In addition to all four of the canonical deoxynucleotides (dATP, dCTP, dGTP and dTTP), a 2',3'-dideoxynucleotide is also included in each in vitro DNA synthesis reaction at a concentration that will result in random substitution of a small percentage of a canonical nucleotide by the corresponding dideoxynucleotide. Thus, each DNA synthesis reaction yields a mixture of DNA fragments of different lengths corresponding to chain termination wherever the dideoxynucleotide was incorporated in place of the normal deoxynucleotide. The DNA fragments are labelled, either radioactively or non-radioactively, by one of several methods and the label(s) may be incorporated into the DNA by extension of a labelled primer, or by incorporation of a labelled deoxy or dideoxy nucleotide. By carrying out DNA synthesis reactions for each of the four dideoxynucleotides (ddATP, ddCTP, ddGTP or ddTTP), then separating the products of each reaction in adjacent lanes of a denaturing polyacrylamide gel, and detecting those products by one of several methods, the sequence of the DNA template can be read directly.

Cycle Sequencing is a variation of Sanger sequencing that achieves a linear amplification of the sequencing signal by using a thermostable DNA polymerase and repeating chain terminating DNA synthesis during each of multiple rounds of denaturation of a template DNA (e.g., at 95° C.), annealing of a single primer oligonucleotide (e.g., at 55° C.), and extension of the primer (e.g., at 70° C.).

Nucleic acid sequencing provides the highest degree of certainty as to the identity of a particular nucleic acid. Also, nucleic acid sequencing permits one to detect mutations in a gene even if the site of the mutation is unknown. Sequencing data may even provide enough information to permit an estimation of the clinical significance of a particular mutation or of a variation in the sequence.

In order to characterize a nucleic acid by sequencing, the nucleic acid must be isolated in sufficient quantity to be used for the particular method. Although it may be possible to obtain sufficient quantities of a nucleic acid for sequencing by first cloning it into a plasmid or other vector, this procedure is time-consuming and is often not practical for routine analysis of samples for clinical diagnostics or other purposes. When the amount of nucleic acid in a sample is less than optimal for a given method, it may be advantageous to use one of several methods which have been developed for amplifying parts of nucleic acid molecules. The polymerase chain reaction (PCR), nucleic acid sequence-based amplification (NASBA), self-sustained sequence replication (3SR), transcription-mediated amplification (TMA) and strand displacement amplification (SDA) are examples of some of the methods which have been developed for amplifying nucleic acid molecules in vitro.

By way of example, a specific portion of a DNA molecule may be amplified using PCR by temperature cycling of a sample DNA in a buffer containing two primers (one primer complementary to each of the DNA strands and which, together, flank the DNA sequence of interest), a thermostable DNA polymerase, and all four canonical 2'-deoxynucleoside-5'-triphosphates (dATP, dCTP, dGTP and dTTP). The specific nucleic acid sequence is geometrically amplified during each of about 30 cycles of denaturation (e.g., at 95° C.), annealing of the two primers (e.g., at 55° C.), and extension of the primers by the DNA polymerase (e.g., at 70° C.), so that up to about a billion copies of the nucleic acid sequence are obtained. RNA may be similarly amplified using one of several protocols for RT-PCR, such as, for example, by carrying out the reaction using a thermostable DNA polymerase which also has reverse transcriptase activity (Myers and Gelfand, 1991).

The polymerase chain reaction (PCR), as discussed above, is the subject of numerous publications, including Mullis, KB, et al., U.S. Pat. No. 4,683,202 and U.S. Pat. No. 4,683,195; Mullis, KB, EP 201,184; Ehrlich, H., EP 50,424, EP 84,796, EP 258,017, & EP 237,362; Ehrlich, H., U.S. Pat. No. 4,582,788; Saiki, R., et al., U.S. Pat. No. 4,683,202; Mullis, KB, et al. (1986) in Cold Spring Harbor *Symp. Quant. Biol.* 51:263; Saiki, R., et al. (1985) *Science* 230:1350; Saiki, et al. (1985) *Science* 231:487; and Loh, EY, et al. (1988) *Nature* 335:141.

By way of a second example, all or a specific portion of an RNA molecule may be amplified using NASBA (Fahy, et al., 1991) by isothermal incubation of a sample RNA in a buffer containing two primers (a first primer complementary to the RNA molecule and encoding a promoter sequence for an RNA polymerase and a second primer complementary to the 3'-end of the first cDNA strand resulting from reverse transcription of the RNA molecule), an RNA- and DNA-dependent DNA polymerase which also has RNase H activity (or a separate RNase H enzyme), all four canonical 2'-deoxynucleoside-5'-triphosphates (dATP, dCTP, dGTP and dTTP), an RNA polymerase that recognizes the promoter sequence of the first primer, and all four ribonucleoside-5'-triphosphates (rATP, rCTP, rGTP and rUTP).

A first cDNA strand is synthesized by extension of the first primer by reverse transcription. Then, the RNase H digests the RNA of the resulting DNA:RNA hybrid, and the second primer primes synthesis of the second cDNA strand. The RNA polymerase then transcribes the resultant double-stranded DNA (ds-DNA) molecule from the RNA polymerase promoter sequence, making many more copies of RNA, which in turn, are reverse-transcribed into cDNA and the process begins all over again. This series of reactions, from ds-DNA through RNA intermediates to more ds-DNA, continues in a self-sustained way until reaction components are exhausted or the enzymes are inactivated. DNA samples can also be amplified by other variations of NASBA or 3SR.

Strand Displacement Amplification (SDA) is another isothermal nucleic acid amplification technique (Walker, 1994). SDA is a method of nucleic acid amplification in which extension of primers, displacement of single stranded extension products, annealing of primers to the extension products (or the original target sequence) and subsequent extension of the primers occurs concurrently in the reaction mix. This is in contrast to the PCR, in which the steps of the reaction occur in discrete phases or cycles as a result of the temperature constraints of the reaction. SDA is based upon 1) the ability of a restriction endonuclease to nick the unmodified strand of a hemiphosphorothioate form of its double-stranded recognition site and 2) the ability of certain polymerases to initiate replication at the nick and displace the downstream non-template strand. After an initial incubation at increased temperature (about 95° C.) to denature double-stranded target sequences for annealing of the primers, subsequent polymerization and displacement of newly synthesized strands takes place at a constant temperature (usually about 37° C.). Production of each new copy of the target sequence consists of five steps: 1) binding of amplification primers to an original target sequence or a displaced single-stranded extension product previously polymerized, 2) extension of the primers by exonuclease deficient (exo$^-$) klenow polymerase incorporating an α-thio deoxynucleoside triphosphate, 3) nicking of a hemiphosphorothioate double-stranded restriction site, 4) dissociation of the restriction enzyme from the nick site, and 5) extension from the 3'-end of the nick by exo$^-$ klenow with displacement of the downstream non-template strand. Nicking, polymerization and displacement occur concurrently and continuously at a constant temperature because extension from the nick regenerates another nickable restriction site. When primers which hybridize to both strands of a double-stranded target sequence are used, amplification is exponential, as the sense and antisense strands serve as templates for the opposite primer in subsequent rounds of amplification.

PCR, NASBA and the other methods of nucleic acid amplification can be very useful for obtaining greater quantities of a nucleic acid for additional characterization. However, in general, the amplified nucleic acid molecules must be purified away from primers, nucleotides, incomplete amplification products and other impurities prior to being used for sequencing. Otherwise, for example, the PCR primers may compete with labelled sequencing primers and the PCR nucleotides may compete with the sequencing nucleotide mixes that are used for Sanger dideoxy sequencing. Also, Sanger sequencing clearly can not be done at the same time as PCR or another amplification method, at least not efficiently, because the dideoxynucleotides used for sequencing will result in termination of the DNA amplification reactions as well as the sequencing reactions.

One group has developed a method that attempts to decrease the number of steps required for sequencing nucleic acids (Shaw and Porter, PCT WO 95/06752). According to this method, 5'-alpha-borano-deoxynucleoside triphosphates, which were found to be resistant to exonuclease III (exo III) digestion, were incorporated into DNA during in vitro DNA synthesis in lieu of one of the canonical nucleotides (dATP, dCTP, dGTP, dTTP) in one of four primer extension reactions. Treatment with exo III will digest the synthesized DNA up to the point of alpha-borano deoxynucleoside incorporation. After digestion with exo III and resolution of the labeled fragments on a polyacrylamide gel, the sequence of the nucleic acid can determined.

An advantage of the alpha-borano/exo III method is that it can be integrated into PCR amplification. However, there are also disadvantages. A key disadvantage is a lower degree of accuracy of the sequence data compared to Maxam-Gilbert or Sanger sequencing because the alpha-borano/exo III method gives both extra bands and missing bands on sequencing gels. Although the mechanism by which these sequencing artifacts are generated is still uncertain, the extra bands may be due to incomplete digestion of non-boronated regions of DNA by exo III, while missing bands may be due to preferential digestion by exo III through some sequences containing alpha-borano-nucleotides. Another serious disadvantage of the alpha-borano/exo III method is related to the substrate requirements of exo III. Because exo III digests only double-stranded DNA, beginning at the 3'-end of each strand, the sequence can only be determined for the 3'-half of each strand of a PCR product, so it is not possible to obtain the sequence near to the primer. Also, because exo III digestion yields only fragments that are between 50% and 100% of the length of the full-size PCR product, the size range of the DNA which can be sequenced by the method is somewhat limited. For example, if a PCR product of 1000 base pairs in length is sequenced according to the alpha-borano/exo III method, the fragments to be electrophoresed would be approximately 500–1000 nucleotides long. Fragments of such a length are more difficult to resolve in DNA sequencing gels.

Uracil N-Glycosylase

"Uracil N-glycosylase" or "uracil-DNA glycosylase" (UNG or UDG) is an enzyme that catalyzes the cleavage of the N-glycosidic bond between the base uracil and the sugar deoxyribose in DNA into which the non-canonical nucleotide 2'-deoxyuridine-5'-triphosphate (dUTP) has been incorporated in place of the canonical nucleotide dTTP (Lindahl, 1979). UDG does not catalyze cleavage of uracil from free dUTP, free deoxyuridine or RNA (Duncan, 1981).

U.S. Pat. No. 5,035,996 describes a process in which UDG is used for controlling contamination of nucleic acid amplification reactions (Hartley, U.S. Pat. No. 5,035,996).

The purpose of this invention was to pretreat reaction mixtures containing a new sample on which an amplification is to be carried out with UDG to assure that any uracil-containing DNA from a prior amplification of another sample had been destroyed and would not contaminate the second amplification reaction. Digesting the second amplification mixture with UDG prior to carrying out the second amplification reaction destroys the ability of any residual products of the first amplification from serving as a template for further amplifications.

Somewhat similarly, U.S. Pat. No. 5,418,149 discloses the use of glycosylases to reduce non-specific amplification of nucleic acids.

A method for introducing site-specific mutations into DNA has also been described that relies upon replacement of thymine with uracil in DNA and subsequent treatment with uracil-DNA glycosylase. See U.S. Pat. No. 4,873,192 and Kunkel, 1985. Also, uracil-containing phage were suggested as a part of a biological containment system that would transfer genetic information only to uracil-N glycosylase deficient cells and not to naturally occurring bacteria. See Warner, et al., 1979.

Another use for UDG in molecular biology has been described by Nisson, et al., 1991. In Nisson, et al. UDG is used to facilitate directional cloning of PCR products. Thus, primers to be used for PCR amplification are made to contain a specific 12-base 5' sequence that contains dUMP in place of dTMP. Then, after the PCR amplification (without dUTP in the reaction mixture), since the amplification products contain dUMP residues at each 5' terminus, treatment of these PCR products with UDG removes the uracil residues from the 5' termini. Subsequent treatment with heat results in cleavage of the phosphodiester bonds at the abasic sites where uracil has been lost and thereby, generates 12-base cohesive termini which can be easily cloned into vectors with complementary termini.

What is needed in the art is a method for characterizing nucleic acids that is as accurate and as specific as Maxam-Gilbert or Sanger sequencing in detecting and identifying nucleic acids and differences between nucleic acids, but that is easier, faster, more sensitive and/or requires less sample DNA. The new method should also be capable of being used for relatively impure nucleic acid samples, such as amplification products, without needing to purify the sample away from primers, nucleotides or other impurities. The method also should be capable of being integrated into an amplification method such as PCR in a way similar to the alpha-borano/exo III method, but without having the disadvantages of the latter method.

SUMMARY OF THE INVENTION

The present invention provides a simple, reliable method for characterizing nucleic acid polymers. In one embodiment, the invention permits the detection and localization of mutations in nucleic acid polymers. In another embodiment, the present invention allows one to determine whether nucleic acid molecules are similar or different and the degree of similarity or difference. In another embodiment, the invention permits one to determine the sequence of a nucleic acid molecule. Because the sequence-delimiting non-canonical nucleotides used for the method are not chain terminators for DNA synthesis, the method may also be part of or coupled to an amplification method such as PCR, NASBA, or SDA.

In the present invention, a DNA molecule is synthesized in the presence of a nucleic acid template, a primer, a polymerase and a non-canonical deoxynucleoside triphosphate as well as all four canonical deoxynucleoside triphosphates. The in vitro synthesized DNA is then treated with an enzyme that excises the non-canonical base from the DNA, whereby an abasic site is created. One then breaks the phosphodiester bonds of the synthesized DNA at the abasic sites and a series of molecules of different lengths is generated.

Each size class of molecule corresponds to the site where a non-canonical nucleotide substituted for the canonical nucleotide within the original sequence. Size resolution of the nested sets of cleaved DNA molecules by gel electrophoresis, capillary electrophoresis, or another method shows the position of individual substitutions by non-canonical nucleotides.

In one embodiment, the non-canonical deoxynucleoside triphosphate is dUTP. The enzyme that excises the non-canonical residue is preferably an N-glycosylase, such as uracil N-glycosylase.

In one embodiment of the present invention, the nucleotide sequence of a DNA molecule is deduced by creating four different reactions in which four different non-canonical deoxynucleoside triphosphates substitute for a portion of each of the canonical deoxynucleoside triphosphates and comparing the products of the reactions.

It is an object of the present invention to compare nucleic acid molecules at the nucleotide level.

It is another object of the present invention to provide a method to detect mutations.

It is another object of the present invention to provide a method of incorporating a non-canonical deoxynucleoside triphosphate that may be compatible with amplification procedures.

It is another object of the present invention to provide a method of determining the sequence of a nucleic acid molecule.

It is another object of the present invention to provide a method to directly sequence amplification products.

It is an advantage of the present invention that the method is accurate and reproducible.

It is another advantage of the present invention that the method does not result in artificial results, such as missing or duplicated bands.

Other advantages, features and objects of the present invention will become apparent after examination of the specification, claims and drawings.

DETAILED DESCRIPTION OF THE INVENTION

Definitions:

The term "mutation", as used herein, refers to alterations in the nucleotide composition of a nucleic acid, and may consist of deletions, insertions, single and multiple residue changes in nucleic acid sequence. These changes normally consist of the substitution of a nucleotide residue by another species of commonly-occurring (canonical) nucleotide.

"Nucleotide" refers to a base-sugarphosphate compound. Nucleotides are the monomeric subunits of both types of nucleic acid polymers, RNA and DNA. "Nucleotide" refers to ribonucleoside triphosphates, rATP, rGTP, rUTP and rCTP, and deoxyribonucleoside triphosphates, such as dATP, dGTP, dTTP, dCTP. "Nucleoside" refers to a base-sugar combination without a phosphate group. "Base" refers to the nitrogen-containing base, for example adenine (A), cytidine (C), guanine (G) and thymine (T).

"Incorporation" refers to becoming a part of a nucleic acid polymer. There is a known flexibility in the terminology about incorporation of nucleic acid precursors. For example, the nucleotide dGTP is a deoxyribonucleoside triphosphate. Upon incorporation into DNA, it becomes a dGMP, or deoxyguanosine monophosphate moiety. Although there is no dGTP molecule in DNA, one may say that one incorporates dGTP into DNA.

The term "canonical" is used to refer to the four common nucleic acid bases adenine, cytosine, guanine and thymine that are commonly found in DNA or to the respective deoxyribonucleosides, deoxyribonucleotides or 2'-deoxyribonucleoside-5'-triphosphates that contain a canonical base. The term "non-canonical" is used to refer to nucleic acid bases in DNA other than the four canonical bases, or to the respective deoxyribonucleosides, deoxyribonucleotides, or 2'-deoxyribonucleoside-5'-triphosphates that contain a non-canonical base. Although uracil is a common nucleic acid base in RNA, uracil is a non-canonical base in DNA. "Non-canonical bases" are found in nucleic acids as a result of incorporation of non-canonical nucleotides or as a result of modification of existing bases (canonical or non-canonical).

The term "amplicon" has come to describe the product of amplification by the PCR or by other nucleic acid amplification techniques known to those skilled in the art.

All temperatures described herein are expressed in degrees centigrade, unless otherwise specified.

In General

Figure 1:
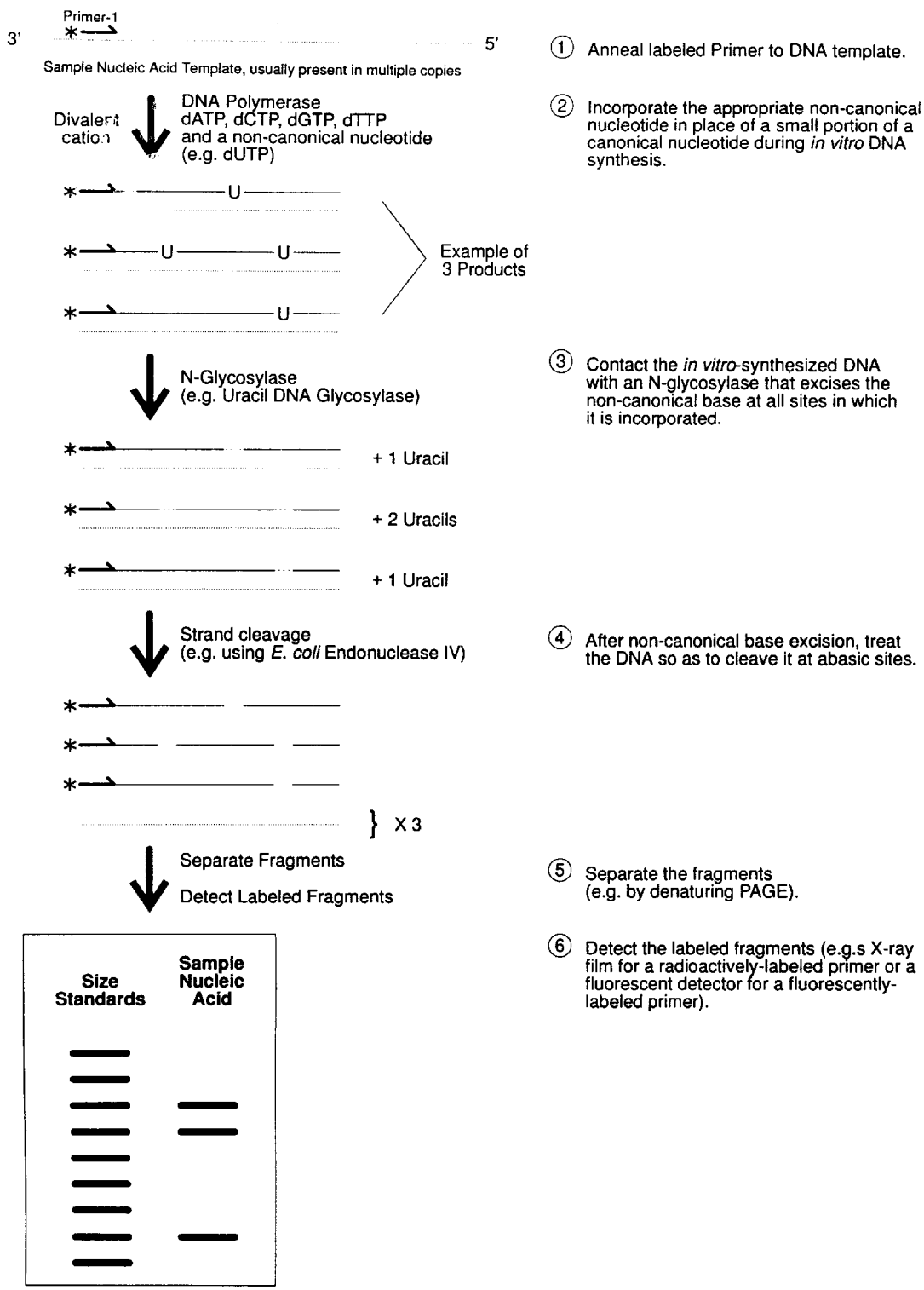
FIG. 1 is a schematic diagram of the BESS method.

We disclose a new method, referred to as "Base Excision Sequence Screening" or "BESS™", for characterizing nucleic acids. FIG. 1 describes an embodiment of BESS.

The BESS method is based on the incorporation of non-canonical nucleotides into DNA during in vitro DNA synthesis using the nucleic acid to be characterized as a template. Referring to FIG. 1, a labelled primer is annealed to a nucleic acid template in the presence of a polymerase capable of extending the primer, all four canonical deoxynucleoside triphosphates and a non-canonical nucleotide. The specific non-canonical nucleotide demonstrated as an example in FIG. 1 is dUTP. Following DNA synthesis, each non-canonical base is excised from DNA by an enzyme specific for that base. In the FIG. 1 example, this enzyme is uracil DNA glycosylase.

Still referring to FIG. 1, the DNA chain is then broken at the abasic sites corresponding to the positions of each non-canonical nucleotide. In FIG. 1, the example demonstrated was the use of an AP endonuclease, Endonuclease IV, to break the DNA at abasic sites. Then, separation of the resulting DNA fragments yields patterns of fragments that end at the positions where non-canonical bases were removed. The positions of each non-canonical nucleotide within the in vitro-synthesized DNA correspond to the positions of a canonical nucleotide within the nucleic acid being characterized.

Figure 2:
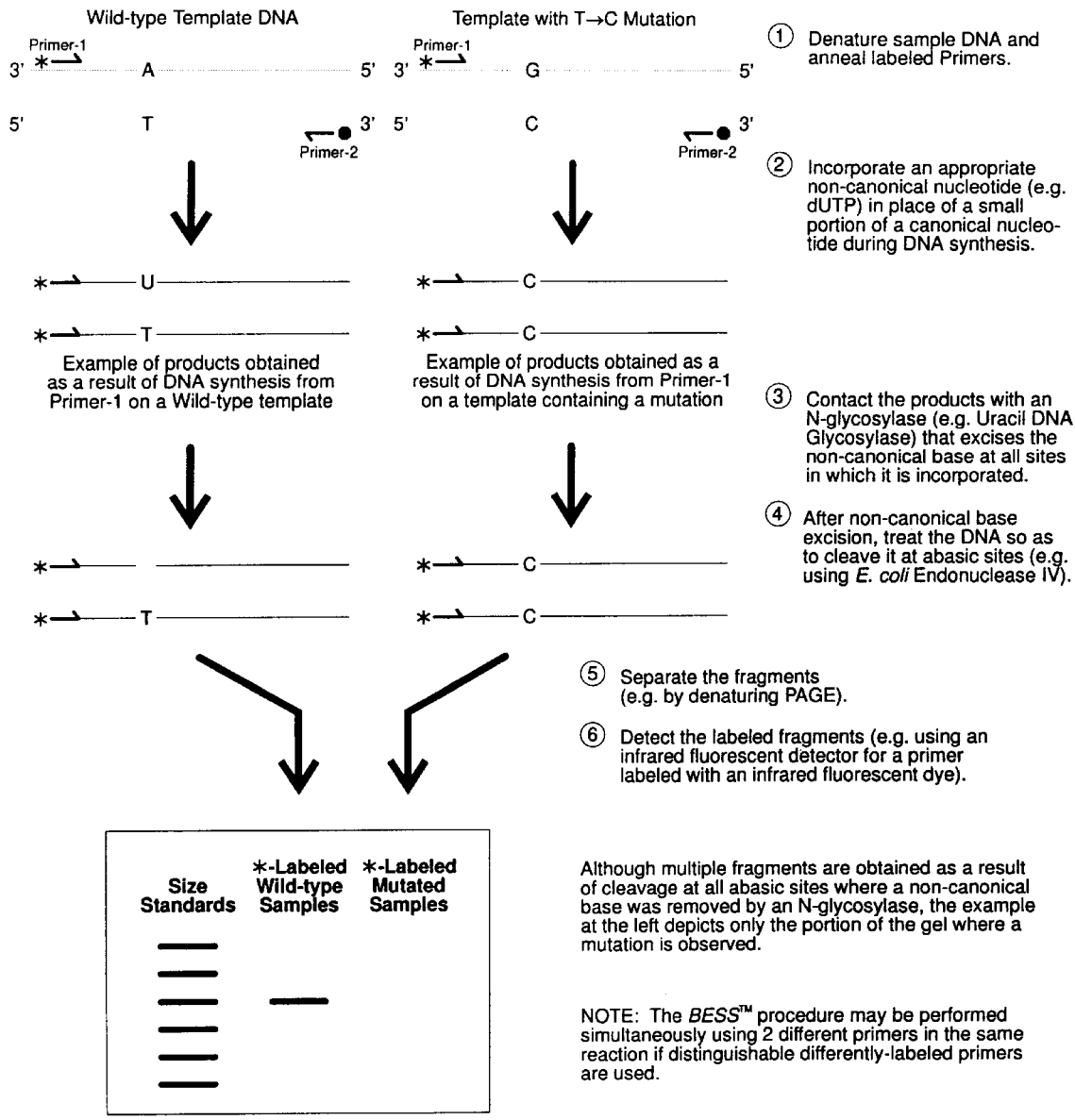
FIG. 2 is a schematic diagram showing the use of BESS to evaluate specific mutation events.
Figure 4:
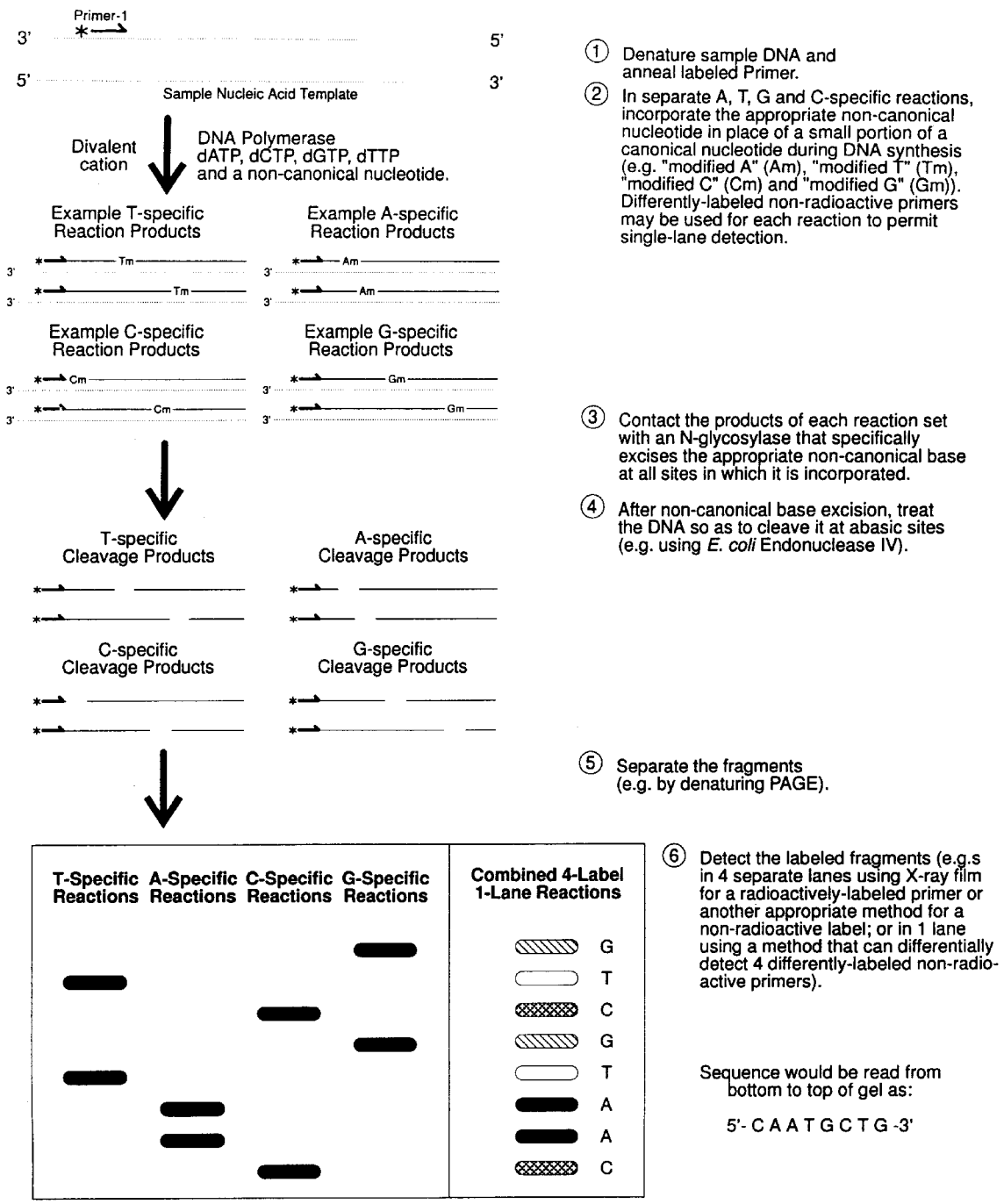
FIG. 4 is a schematic diagram of DNA sequencing using BESS.
Figure 5:
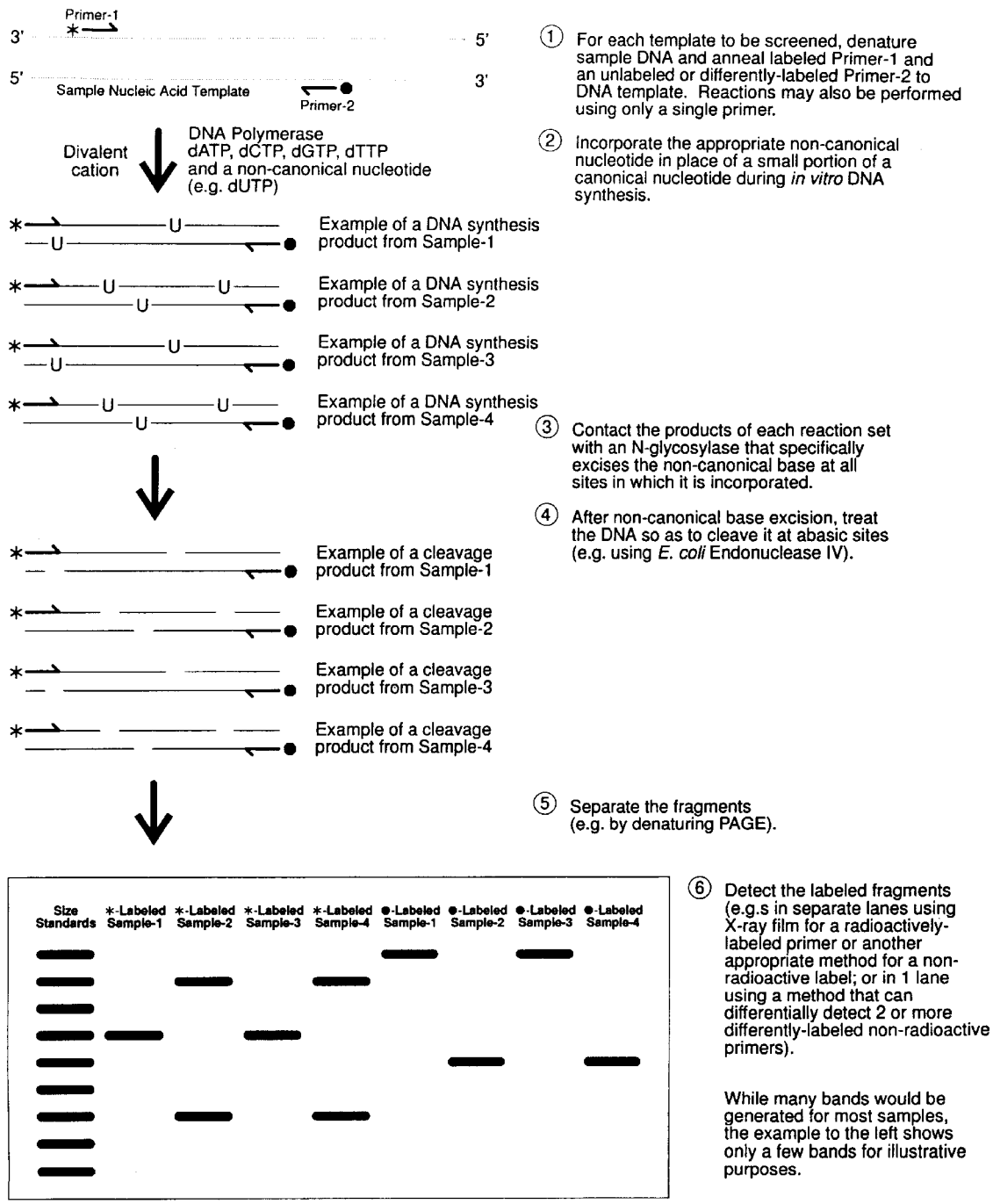
FIG. 5 is a schematic diagram showing the use of BESS to determine if and to what extent nucleic acid molecules are similar or different.

BESS, even when applied to a single non-canonical nucleotide, may be used to obtain a sequence-related pattern of DNA fragments in order to characterize either the presence or absence of a particular nucleic acid sequence or its relatedness to another nucleic acid sequence (see FIGS. 2 and 5). Because non-canonical nucleotides used for BESS do not terminate the DNA chain, BESS may be part of an amplification process such as PCR, RT-PCR, NASBA, or SDA, or any other method involving in vitro DNA synthesis (see FIG. 3). BESS may also be used to determine the complete nucleotide sequence of a nucleic acid molecule (see FIG. 4).

A preferred method for DNA synthesis during the BESS reaction is described in *PCR Technology,* Griffin and Griffin, eds., CRC Press, Boca Raton, Fla. (1994). The preferred minimal components for synthesis of DNA are: a template DNA (double- or single-stranded), a primer oligodeoxynucleotide of a sequence which is the reverse complement of a portion of the template, the four canonical deoxynucleoside triphosphates at a concentration of 50–250 micromolar, a buffer of pH 6.5–9.0, magnesium ions at 1–10 mM, and a DNA polymerase enzyme. The concentration of the non-canonical deoxynucleoside triphosphate and its proportion in the reaction mixture with respect to the corresponding canonical nucleotide are determined empirically for each non-canonical nucleotide and DNA polymerase combination. The present invention requires the incorporation of a quantity of non-canonical nucleotide such that, for any given site along the polynucleotide, only a fraction of all molecules will be cleaved at that site by an N-glycosylase enzyme. The non-canonical nucleotide may be a specific substitute for any of the four common nucleotide components for synthesizing DNA: deoxythymidine triphosphate, deoxyadenosine triphosphate, deoxycytosine triphosphate, or deoxyguanosine triphosphate. Some preferred methods are described in the Examples below.

In the BESS method, the incorporation of the non-canonical nucleotide occurs during a standard DNA synthesis reaction. Either a DNA or RNA molecule may serve as the template. Those of skill in the art know of many modifications of this reaction. Preferably, the reaction is performed with a labelled primer containing a nucleotide sequence at least part of which is sufficiently complementary to a portion of the template molecule to hybridize with the template. If the template is a DNA molecule, preferably a DNA-dependent DNA polymerase extends the primer molecule. Most preferably, this DNA-dependent DNA polymerase is a thermostable DNA-dependent DNA polymerase. If an RNA molecule is the template, an RNA-dependent DNA polymerase (reverse transcriptase) is used. Preferably, this enzyme is thermostable.

A radioactively-labelled primer enables one to visualize the reaction product by exposing the separated reaction products to an X-ray film. Alternatively, one may label the primer and detect the reaction products by non-radioactive methods known to one of skill in the art.

dUTP as the Non-Canonical Nucleotide

In one embodiment of the invention, the non-canonical nucleotide dUTP is incorporated into a DNA sequence during DNA synthesis. The BESS method and some of its uses are illustrated in the figures using dUTP as an exemplary non-canonical nucleotide and uracil-DNA glycosylase as an exemplary N-glycosylase. For example, a specific mutation involving the loss or gain of a deoxythymidine (dT) residue may be detected after the incorporation of deoxyuridine (dU) into the DNA. Digestion of the dU-substituted sample with UDG and hydrolysis of the phosphodiester bonds at the abasic sites (points of dU removal) leads to a nested set of fragments ending at each of the abasic sites. In this embodiment, the loss or gain of a dT residue by mutation must occur on the same strand of the nucleic acid which will be detected following gel electrophoresis or another separation method.

The incorporation may be during a PCR or another amplification involving DNA synthesis known to the art. A mixture of deoxynucleotides dGTP, dCTP, dATP, dTTP and dUTP is used as the precursor pool for incorporation into newly synthesized DNA. Although the nucleotide incorporated opposite a dA on the template strand is dT for the majority of the synthesized DNA molecules, dU constitutes the nucleotide at any such position for a fraction of the DNA molecules synthesized.

The synthesized nucleic acid is then treated with an N-glycosylase, such as UDG, which removes only uracil from such sites where it has been incorporated as dU. This removal creates an "abasic" site. Because uracil is present in only a fraction of the possible incorporation sites, the nucleic acid is cleaved by UDG at that position in a fraction of the molecules. If dU is randomly incorporated into the nucleic acid at sites normally containing dT, UDG digestion and phosphodiester bond scission generates a collection of molecules differing in length by the distance between dT residues in the original nucleic acid sequence. Such a nested set of molecules may then be resolved by electrophoretic separation means, and the precise location of the dT residues in the original nucleic acid may be inferred.

Mutation Analysis

FIG. 2 describes the use of the BESS technique to examine specific mutations. Specifically, FIG. 2 shows an example in which a mutation results from substitution of a single T residue in wild-type DNA by a C residue in mutated DNA. This change is detected using BESS as the loss of band on a PAGE gel for the sample with mutated DNA compared to the sample with wild-type DNA.

Referring to FIG. 2 both the wild-type DNA and the mutated DNA are denatured and annealed with labelled primers. The strand complementary to the one containing the T-to-C transition serves as the template for DNA synthesis. An appropriate non-canonical nucleotide is incorporated during the DNA synthesis reaction in place of a small portion of a canonical nucleotide. FIG. 2 describes the products of the wild-type template and a template with an A-to-G mutation.

Still referring to FIG. 2, the products are exposed to an appropriate N-glycosylase. The N-glycosylase will excise the non-canonical base at all sites in which it is incorporated. The DNA is then treated so as to cleave it at the abasic sites and the fragments are separated. FIG. 2 illustrates the result of comparing the labelled reaction products from the wild-type samples and the labelled reaction products from the mutated samples. Multiple fragments will be obtained as a result of cleavage at all abasic sites where a non-canonical base was removed by an N-glycosylase. The example shown in FIG. 2, depicts only the portion of the electrophoretic gel where a mutation is observed.

If the above process is carried out using either (1) two PCR primers with different detection labels or (2) two separate PCR mixtures, each carried out with a different one of the two PCR primers labelled, the position of dT in both strands of DNA may be determined.

As seen in Table 1, ten out of twelve possible base substitution mutations of DNA involve the loss or gain of a T on one or the other strand. Therefore, an embodiment of the invention using dUTP as the non-canonical nucleotide can be used to locate most point mutations. Table 1 compares various mutations and detection of the mutation after UDG digestion.

TABLE 1

Detection of single-base substitution mutations using two differently-labelled PCR primers

| MUTATION IN SENSE STRAND | SENSE STRAND PRIMER | ANTI-SENSE PRIMER | MUTATION DETECTED after UDG |
|---|---|---|---|
| A→ G | — | lose T | YES |
| A→ C | — | lose T | YES |
| A→ T (U) | gain T | lose T | YES |

TABLE 1-continued

Detection of single-base substitution mutations using two differently-labelled PCR primers

| MUTATION IN SENSE STRAND | SENSE STRAND PRIMER | ANTI-SENSE PRIMER | MUTATION DETECTED after UDG |
|---|---|---|---|
| G→ C | — | — | NO |
| G→ T (U) | gain T | — | YES |
| G→ A | — | gain T | YES |
| C→ T (U) | gain T | — | YES |
| C→ A | — | gain T | YES |
| C→ G | — | — | NO |
| (U) T→ A | lose T | gain T | YES |
| (U) T→ G | lose T | — | YES |
| (U) T→ C | lose T | — | YES |
| | 6/12 detected with one primer | 6/12 detected with one primer | 10/12 detected with two primers |

Thus, ten out of twelve possible point mutations may be determined with great sensitivity by coupling an embodiment of the present invention using dUTP incorporation and UDG digestion and PCR with two different labelled primers. With one primer labeled, one-half (6 out of 12) of the possible mutations could be determined using this embodiment of the invention. The detection of the other two mutations, dG to dC and dC to dG, requires the use of non-canonical nucleotides that specifically substitute for dG or for dC, and N-glycosylases which remove each respective non-canonical base. Both of these mutations could be detected using only one non-canonical nucleotide, substituting for dGTP or dCTP, and one corresponding N-glycosylase if two different labelled primers were used (one for priming each strand of a DNA template).

Use of Other Non-Canonical Nucleotides

For embodiments of the invention involving non-canonical nucleotides other than dUTP, it is necessary that one select N-glycosylases which will selectively cleave the respective non-canonical base from the synthesized DNA strand. There are other N-glycosylases known to the art (Demple and Harrison, 1994 and Lindahl, 1979) which may be utilized to remove specific non-canonical nucleotides from DNA. Table 2 lists some of these enzymes.

deoxynucleotide must not either terminate the extension of the product DNA strand or cause the polymerase to falter or result in a mutation on the complementary strand. In some cases, the presence of an unusual non-canonical nucleotide may alter the DNA synthesis reaction or the physical properties of the DNA into which it is incorporated so that DNA synthesis parameters need to be optimized.

There are several other general requirements envisioned for the invention. The non-canonical nucleotide must be obtainable by some means, such as by chemical synthesis, by degradation of polynucleotides, by enzymatic modification of nucleotides, or by a combination of these processes, and the product of said process or processes must then be converted into a deoxynucleoside triphosphate. Additionally, there must be a specific N-glycosylase to excise the non-canonical base from a nucleic acid into which it is incorporated.

There are variations of the invention envisioned which allow for the position of canonical nucleotides to be specifically determined without direct incorporation during DNA synthesis of the non-canonical nucleotide recognized by the N-glycosylase. Thus, canonical or non-canonical nucleotides in DNA are first specifically converted to non-canonical nucleotides which are specific substrates for appropriate glycosylase enzymes. Such a conversion to a non-canonical nucleotide recognized specifically by an N-glycosylase may be accomplished by chemical or enzymatic means. The phosphodiester bonds at the abasic sites generated by glycosylase activity are then broken as described herein. For example, DNA with abasic sites may be prepared by deamidation of cytosine followed by treatment with UNG (Sagher and Strauss, 1985).

Use of N-Glycosylases

Other specific N-glycosylases will become available and known to those of skill in the art. In order to determine whether or not an N-glycosylase is suitable for the present invention, one would first incorporate the non-canonical nucleotide into the synthesizing DNA and determine whether or not the non-canonical base can be specifically removed by the candidate N-glycosylase. The example above, describing the use of UDG, would serve as a comparative control.

TABLE 2

| CANONICAL BASE in DNA | NON-CANONICAL NUCLEOTIDE | NON-CANONICAL NUCLEOTIDE REFERENCE | GLYCOSYLASE | SOURCE OF GLYCO-SYLASE | GLYCO-SYLASE REFERENCE |
|---|---|---|---|---|---|
| T (thymine) | dUTP (deoxyuridine triphosphate) | Bessmans, et al., 1958 | UDG or UNG | E. coli | Lindahl, 1974 |
| G (guanine) | dITP (deoxyinosine triphosphate) | Thomas, et al., 1978 | HXNG (hypoxanthine-N-glycosylase) | a) calf thymus b) E. coli | Karran and Lindahl, 1980 Karran and Lindahl, 1978 |
| C (cytosine) | 5-OHMe-dCTP (5-hydroxymethyl deoxycytidine triphosphate) | Stahl and Chamberlin, 1976 | hydroxy-methyl cytosine-N-glycosylase | calf thymus | Cannon, et al., 1988 |

A non-canonical deoxynucleotide of the present invention must be incorporated into DNA with fidelity and must be compatible as a component of product DNA during subsequent rounds of DNA synthesis. That is, the non-canonical By "N-glycosylase" or "DNA-glycosylase" we mean an enzyme with N-glycosylase activity, whether or not the enzyme is formally called a glycosylase or has a glycosylase activity combined with other enzymatic activities. Glycosylases are sometimes referred to as "glycosidases," and we therefore mean the definition of N-glycosylase to cover N-glycosidases.

As defined herein, an N-glycosylase or DNA glycosylase is an enzyme that catalyzes hydrolysis of the bond between a non-canonical nucleic acid base and a sugar in DNA to generate an abasic (AP) site. Such enzymes are present in many species. An example from *Escherichia coli* is uracil-DNA glycosylase (UDG), also called uracil N-glycosylase (UNG). Other examples are described by Demple and Harison (1994) and by Duncan (1981).

Cleavage at the Abasic Site

Once one has created an abasic site, the method of the present invention requires that the synthesized DNA strand be cleaved at this site. There are various methods known to those of skill in the art to cleave an abasic site. Heat and/or basic conditions may be used to break the DNA molecule at the abasic sites. For example, the following protocol may be used: Nucleic acids containing abasic (AP) sites following removal of non-canonical bases are heated in a buffer solution containing an amine, for example, 25 mM Tris-HCl and 1 to 5 mM magnesium ions, for a period of 10 to 30 minutes at 70° C.–95° C. Alternatively, the following treatment may be used to break the DNA at abasic sites: 1.0 M piperidine, a base, is added to DNA which has been precipitated with ethanol and vacuum dried. The solution is then heated for 30 minutes at 90° C. and lyophilized to remove the piperidine.

Preferably, enzymatic treatment is used to break the DNA polymer at the abasic site. For example, apurinic/apyrimidinic endonucleases (AP endonucleases) have been described which are able to cleave the phosphodiester bonds of DNA at apurinic or apyrimidinic (AP) sites (Lindahl, 1979; Demple and Harrison, 1994).

The employment of AP endonucleases such as Endonuclease IV from *E. coli* appears to be the preferred method of phosphodiester bond cleavage. As defined herein, an AP endonuclease is any enzyme that catalyzes cleavage of DNA at abasic (AP) sites. Such enzymes are present in many species. Examples of AP endonucleases from *Escherichia coli* include, but are not limited by, endonuclease III and endonuclease IV. Also, *E. coli* exonuclease III in the presence of calcium ions is an AP endonuclease. Enzymes useful in the present invention include any enzyme with AP endonuclease-like activity, whether it is called by that name or by some other name.

Endonuclease IV cleaves between the 5'-phosphate group of the AP residue and the deoxyribose ring of the adjacent nucleotide, generating a free 3'-hydroxyl group. In contrast to AP endonuclease-catalyzed cleavage, pyrolysis of the phosphodiester bond may occur on either side of the AP residue, producing a mixture of 3'-phosphorylated ends on the cleavage products. Thus, the result of AP DNA cleavage with an AP endonuclease, such as Endonuclease IV, is a set of sharper bands after electrophoresis than is obtainable with pyrolysis.

Examination of BESS Products

Once cleavage has occurred at the abasic sites, one would wish to resolve the BESS products. Preferably, this resolution will be by gel electrophoresis or capillary electrophoresis. Then, the sizes of the fragments will be visualized either by staining the DNA molecules or by exposing radioactively labelled DNA molecules to X-ray film. The fragments may likewise be visualized using non-radioactive detection methods known to those of skill in the art. The reaction products from 1, 2, 3, 4 or more BESS reactions may be visualized in the same lane of an electrophoresis gel or a single capillary if different distinguishable non-radioactive labels are used for each reaction.

A suggested protocol for electrophoresis of the BESS fragments is: a 0.2–0.4 mm gel of 6 or 8% polyacrylamide, 89 mM tris-borate, pH 8.3, 1 mM EDTA (TBE buffer) and 7 M urea is used to separate DNA fragments. Denaturing loading buffer (95% formamide, 0.1% bromophenol blue, 0.1% xylene cyanol and 10 mM EDTA, pH 7.6) is added to samples which were heated at 85–95° for 5 minutes. Then, the samples are electrophoresed at 1200–2500 volts in TBE buffer.

Advantages of BESS Protocol

The BESS method has several advantages. The principal advantage is the ability to characterize nucleic acid molecules at the nucleotide level. This method allows one to select specific regions of DNA or RNA for analysis at the nucleotide level.

Figure 3:
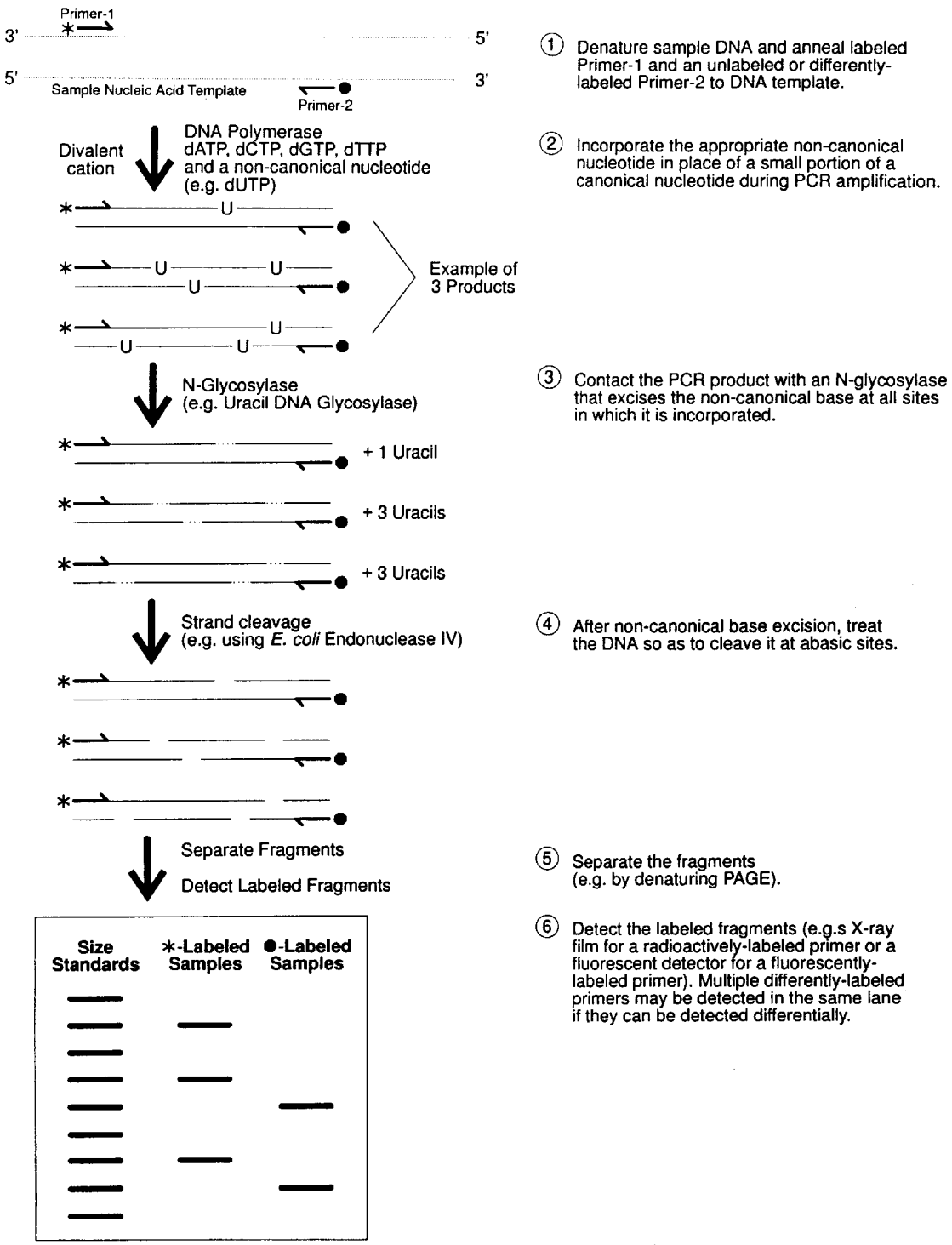
FIG. 3 is a schematic diagram showing coupled PCR and BESS.

FIG. 3 demonstrates the coupling of the BESS protocol with an amplification reaction. Note that FIG. 3 includes the step of incorporation of the non-canonical nucleotide in place of a small portion of a canonical nucleotide during PCR amplification. As described above for non-amplification products, the PCR product is exposed to an N-glycosylase that excises the non-canonical base at all sites in which it is incorporated. The samples are then treated to cleave the strands at the abasic sites. FIG. 3 demonstrates the expected products that would occur after strand cleavage and demonstrates the analysis of the separated fragments.

Another advantage of the invention over current technologies could be the generation of a pattern of bands which may be used to confirm the identity of an amplification product (see FIG. 3, for example). In some cases in the art, a PCR product of the correct molecular size is presumed to be derived from the desired template sequence. The DNA moiety may in fact be the amplification product of another nucleic acid template, and the result is then a "false positive". If the PCR product fragments generated by this invention are compared with a standard set of fragments derived from the sequence in question, they may be positively identified, even if there are mutations present. A mutation is recognizable as a deviation from the normal pattern of bands. The invention may avoid the occurrence of false positive results because the identity of the amplicon may be checked from its characteristic banding pattern after N-glycosylase digestion and phosphodiester bond breakage.

Another advantage of the invention is that the amplification process itself can incorporate non-canonical nucleotides which are then detected in the product.

An especially advantageous feature of the invention is that the amplification product does not require further purification before the positions of the non-canonical nucleotide are determined. Many current methods of sequencing PCR products involve labor-intensive purification steps, followed by an additional single-strand amplification which incorporates label and chain terminating nucleotides. Purification of the amplicon is usually necessary to remove components of the original amplification, such as nucleotides, primers, truncated extension products and unwanted non-specific products of amplification. The present invention eliminates the need for purification steps prior to determining a nucleotide's position in the sequence.

The process described in PCT WO 95/06752 wherein exonuclease III digestion can be used to determine the presence of alpha-borano nucleotide incorporation sites, also enables the direct sequencing of PCR products. However, the process generates extra and missing bands in sequencing gels. Although the reasons for these artifacts are still uncertain, extra bands may be caused by incomplete digestion by exonuclease III (exo III). The present invention utilizes an N-glycosylase to remove specific bases from DNA, which in turn allows chain cleavage at AP sites. Sequencing gel band artifacts common with the WO 95/06752 process should not occur using the current invention.

Use of BESS to Determine Nucleotide Sequence

By incorporating non-canonical deoxynucleoside triphosphates in place of a portion of the four canonical deoxynucleoside triphosphates and by using appropriate N-glycosylase enzymes, the positions of all four canonical nucleoside triphosphates may be determined using the invention. Therefore, the complete sequence of the nucleic acid may be determined using the present invention. In this embodiment, there are separate N-glycosylases to remove each specific non-canonical nucleotide incorporated into a nucleic acid (see FIG. 4). In such a case, there are distinct non-canonical nucleotides incorporated into each of four versions of the nucleic acid. The four versions of the nucleic acid are then separately digested by N-glycosylases specific for each non-canonical nucleotide. After the glycosylase digestion and phosphodiester bond cleavage, the fragments are separated by gel electrophoresis, capillary electrophoresis or other means. Cleavage of the phosphodiester bonds of the sugar-phosphate moiety is carried out by non-enzymatic beta-elimination or by enzymatic means. If each non-canonical nucleotide is a specific substitute for each of the four common nucleotides, the complete sequence of said nucleic acid may be determined.

FIG. 4 describes a method of DNA sequencing in which a labelled primer is first annealed to a denatured sample of DNA. Separate A, T, G and C-specific reactions are created to incorporate an appropriate non-canonical nucleotide in place of a small portion of the canonical nucleotide during DNA synthesis. We note that differently-labelled non-radioactive primers may be used for each reaction to permit single lane detection. Referring to FIG. 4, the symbol Am, Tm, Cm and Gm refer to "modified A," "modified T," "modified C" and "modified G." These "modified bases" are the non-canonical nucleotides.

Still referring to FIG. 4, the products of each nucleotide-specific reaction are then contacted with an N-glycosylase that specifically excises the appropriate non-canonical base at all sites in which it is incorporated. After non-canonical base excision, the products are treated to cleave at the abasic sites, preferably using an AP endonuclease such as *E. coli* endonuclease IV. These fragments may then be separated, preferably by denaturing polyacrylamide gel electrophoresis, by capillary electrophoresis, or by other methods, and analyzed. The sequence of the template molecule may be determined from this comparison, as demonstrated in FIG. 4. FIG. 4 also demonstrates how the sequence can be determined from one-lane electrophoresis if differently labelled non-radioactive primers are used for each reaction.

Alternatively, one could perform all the nucleotide-specific reactions in one large reaction providing that the incorporated non-canonical nucleotides do not cause mutagenic events. This reaction can be aliquoted into separate reactions for treatment with the appropriate N-glycosylase. The products can then be separated and analyzed as before.

Non-canonical nucleotides may be incorporated using cycle sequencing reactions in which each of four parallel reactions contains one non-canonical nucleotide along with the four common nucleotides. Each reaction is then digested by an N-glycosylase specific for the non-canonical nucleotide incorporated. The products obtained after phosphodiester bond breakage may then be resolved using denaturing gel electrophoresis or other methods as previously described.

Use of BESS to Determine Similarities or Differences between Nucleic Acids

Just as the electrophoretic pattern of DNA fragments obtained by digesting an entire DNA molecule with different restriction enzymes can be used to characterize and roughly identify the DNA molecule (by a restriction map), the electrophoretic pattern of DNA fragments generated using the BESS method can be used to characterize and identify nucleic acid molecules at the more precise nucleotide level. Thus, the BESS method, even using a single non-canonical nucleotide and a single N-glycosylase, may be used to determine if and to what extent different nucleic acid samples are similar or different at the nucleotide level.

FIG. 5 demonstrates the use of the BESS method to determine similarities and differences between nucleic acids. The method begins with annealing a labelled primer 1 and an unlabelled or differently labelled primer 2 to a denatured DNA template. (The reaction may also be performed using only a single primer.)

Non-canonical nucleotides are then incorporated in place of a small portion of a canonical nucleotide using in vitro DNA synthesis. FIG. 5 demonstrates examples of synthesis products from four different DNA template samples to be evaluated. The products of each reaction are treated with an N-glycosylase that specifically excises the incorporated non-canonical base at all sites in which it is incorporated. The DNA is then treated so as to cleave at the abasic sites, preferably using an AP endonuclease such as *E. coli* endonuclease IV.

Still referring to FIG. 5, the cleavage products of all four samples are illustrated. These cleavage samples are separated, preferably by denaturing polyacrylamide gel electrophoresis or another method, as described herein, and the labelled fragments are detected. Many bands would be generated from most samples and the FIG. 5 example shows only a few bands for illustrative purposes.

Kit for Characterizing Nucleic Acids

The present invention is also a kit for characterizing nucleic acids. In one embodiment this kit will comprise an enzyme capable of extending a primer which is hybridized to a nucleic acid template, four canonical deoxynucleoside triphosphates, at least one non-canonical deoxynucleoside triphosphate, an N-glycosylase corresponding to each non-canonical nucleotide, and an AP endonuclease. Preferably, the AP endonuclease is Endonuclease IV.

Another form of the kit would be useful for one who was performing characterization on a specific DNA template. In this embodiment of the kit, at least one primer designed to hybridize to a short section of the specific DNA template would be provided in the kit. The kit may also contain other components required to couple BESS with an amplification method. For example, a kit for coupling BESS with PCR amplification of a specific nucleic acid sequence may contain two different primers, labelled and/or unlabelled, which flank the sequence of interest.

In a most preferred embodiment of the kit, the enzyme would be a thermostable DNA polymerase.

Another embodiment of the kit would be designed for DNA sequencing applications. In this embodiment, the kit would contain four different non-canonical nucleotides designed to replace a portion of each of the four different canonical nucleotides and four different N-glycosylases which catalyze specific removal of each of the non-canonical bases following their incorporation into DNA.

Alternatively, the kit could contain only two or three non-canonical nucleotides, if both strands of a specific DNA are to be sequenced.

EXAMPLES

Example 1

This example demonstrates the detection of a single-base mutation of clinical significance using the BESS method. The example also demonstrates coupling of BESS with PCR. Coupling BESS with amplification permits one to obtain results with smaller amounts of sample nucleic acid, which may be limited in some situations.

A polymerase chain reaction (PCR) was performed to amplify a region of the human β-globin gene contained within the plasmids pHB4 or pSic2. The plasmids were constructed by the insertion of a 290 bp segment of the human β-globin gene into the vector pT7Blue (Novagen, Madison, Wis.). The two plasmids differ only by the substitution of an adenosine by a thymidine in the sense strand of the globin gene portion of pSic2. Such a mutation in human DNA is the molecular cause of the $β^S$ or sickle globin defect (Kazazian, 1989). The primers used to amplify the globin gene were the standard forward and reverse M13 sequencing 24-mer oligonucleotides, 5'-CGCCAGGGTTTTCCCAGTCACGAC-3' and 5'-AGCGGATAACAATTTCACACAGGA-3' (SEQ ID NOs:5 and 6), respectively.

100 picograms of plasmid pHB4 or pSic2 DNA was added to PCR reactions of 50 microliters, containing 50 mM Tris-HCl pH 9.0, 20 mM ammonium sulfate, 1.5 mM magnesium chloride, 0.2 mM each of dATP, dCTP, and dGTP, 0.16 mM dTTP, 0.04 mM dUTP, 0.1 microgram of unlabeled forward primer, 0.1 microgram of $^{32}$P-end-labeled reverse primer, and 2.5 units of Tth DNA polymerase or Taq DNA polymerase (Perkin-Elmer Corporation, Branchburg, N.J.). The reactions were heated at 94° for 2 minutes, cycled at 95° for 30 seconds, 55° for 30 seconds, and 72° for 30 seconds for 30 repetitions, and finally held at 4°.

Following the amplification, the sample was treated with one unit of UDG (Epicentre Technologies, Madison, Wis.) at 37° for 20 minutes, and the phosphodiester backbone of the amplicon was cleaved at sites of uridine removal by heating at 70° for 10 minutes. The sample was diluted with 95% formamide, 10 mM EDTA, pH 9.5, 10 mM NaOH and 0.1% each of bromophenol blue and xylene cyanol.

No purification of the reaction products was performed. Rather, the products of the reaction were heat denatured and directly electrophoresed in an 8% polyacrylamide, 8 M urea gel. The gel was fixed, dried and exposed to X-ray film. Parallel samples containing sequencing reactions for the same plasmids were generated using the SequiTherm™ Cycle Sequencing Kit (Epicentre Technologies, Madison, Wis.) according to the manufacturer's directions for a $^{32}$P-end-labeled reverse primer.

The results show that the UDG-digested products of the pHB4 amplicon containing deoxyuridine displays an additional band at the site of the A to T mutation which is characteristic of the sickle globin gene. The corresponding sequences obtained by cycle sequencing were electrophoresed in adjacent lanes for comparison. The UDG-generated lanes have the same pattern of bands as the "T" lane of the cycle sequencing products, except, as expected, the bands from the UDG-treated material migrate slightly faster. The mutation of the sickle gene is also clearly visible in the cycle sequencing lanes. The same results were obtained with either Tth DNA polymerase or Taq DNA polymerase.

Example 2

The following example demonstrates that BESS, coupled with an amplification method, is capable of detecting a clinically-significant single-base mutation, even when the mutation is present in only one allele of a heterozygous individual. The DNA samples used were obtained from humans who were either homozygous for the normal allele or heterozygous for the normal and mutant alleles. The results obtained using BESS were confirmed by sequencing both normal and mutant-containing DNA samples using standard methods.

The alpha$_1$-antitrypsin gene was amplified from human DNA using a protocol similar to that of Example 1. The Z gene mutation of the alpha$_1$-antitrypsin gene is a G-to-A transition in exon five, which leads to an amino acid change of glutamate to lysine at position 342. An embodiment of the present invention was used to detect the Z gene mutation in one allele of a heterozygous MZ individual.

The "M" form of the alpha$_1$-antitrypsin gene is the normal or wild-type condition. Amplification reactions contained one-half microgram of human genomic DNA from apparently normal or MZ alpha$_1$-antitrypsin heterozygous persons (Coriell Institute for Medical Research, Camden, N.J.) as the template in place of plasmid DNA. The primers, 5'-GAGGAGGAGCAAGGCCTATGTG-3' and 5'-GGGATTCACCACTTTTCCCATG-3', (SEQ ID NOs:1 and 2) were chosen to amplify parts of intron four and exon five of the alpha$_1$-antitrypsin gene (Cox, 1990). The reactions contained 50 mM Tris-HCl pH 9.0, 20 mM ammonium sulfate, 1.5 mM magnesium chloride, 0.2 mM each of dATP, dCTP, and dGTP, 0.16 mM dTTP, 0.04 mM dUTP, 0.1 microgram of each of the primers described above, and 2.5 units of Taq DNA polymerase (Perkin-Elmer, Branchburg, N.J.).

The reactions were submitted to 35 cycles consisting of 91° for 1.5 minutes, 55° for 30 seconds, and 68° for 1 minute, then were held at 4°. The amplicons resulting from amplification in the presence of dUTP were treated with UDG and pyrolyzed as described in Example 1.

Without further purification steps, both the UDG-treated amplicons and the cycle sequence reaction samples were electrophoresed in a polyacrylamide-urea gel as described in Example 1. The MZ heterozygous DNA yielded an additional "T" band at the position of the mutation which is one-half the intensity of the other T bands, because only one amplified allele contains the Z mutation. Using BESS, the AAT Z mutation was detectable in the amplification products obtained from a mixture of normal and mutant alleles in chromosomal DNA.

As a control display of the Z mutation, the PCR products of both normal and MZ heterozygote genes were sequenced. Amplicons synthesized without dUTP and containing only the canonical four deoxynucleotides were electrophoresed in a discontinuous 13% polyacrylamide gel containing sodium dodecyl sulfate detergent. The 310 bp amplicon was localized by staining with ethidium bromide, and cut from the gel. The PCR products were purified by crushing and soaking the gel fragment in 0.5 M ammonium acetate, 1 mM EDTA, and 0.1% SDS using methodology known to the art. This DNA was used as the template to generate cycle sequencing data using $^{32}$P end-labeled primers as described in the product information for SequiTherm™ Cycle Sequencing Kits (Epicentre Technologies). Standard cycle sequencing performed as described in Example 1 confirmed the sequence of the normal and mutant DNA samples that were obtained using BESS coupled with PCR.

Example 3

The effectiveness of endonuclease IV digestion of AP DNA generated using BESS is demonstrated in Example 3. As a standard of reference, the T lane of the SequiTherm-sequenced AAT PCR product (Example 2) was compared with the results of BESS in several of its embodiments. The first embodiment was UNG digestion of dU-substituted PCR product (37° for 10 minutes) followed by pyrolysis (90° for 20 minutes) to cleave the phosphodiester bonds at AP sites. The second is the same as the first, except that endonuclease IV was added concurrently with UNG, and no 90° heat step followed. The third is the same as the second, except that EDTA was added to 10 mM final concentration prior to UNG and endonuclease IV addition. Several conclusions may be reached from the experiment:

(1) The products of the pyrolysis of AP DNA result in electrophoretic bands that are less sharp than those resulting from endonuclease IV cleavage of the same amplification product.

(2) The endonuclease IV reaction allows the polymerase to extend, in some cases, the cleavage product 3'-hydroxyl ends, resulting in spurious bands. The addition of a chelating agent such as EDTA before or concurrently with UNG and endonuclease IV prevents the polymerase from extending the cleavage product ends and eliminates the spurious bands.

(3) As expected, the BESS products migrate more rapidly during electrophoresis than the corresponding products from Sanger cycle sequencing reactions using SequiTherm™. The migration difference is more apparent at the bottom of the electrophoresis gel.

(4) Artifactual bands obtained in cycle sequencing of the PCR products were eliminated using the invention. More accurate sequence information may be obtained using the invention in its preferred embodiments than using methods now known to the art.

Example 4

The second exon of the DQB1 gene of the human HLA class II complex is a highly polymorphic region (Bugawan and Ehrlich, 1991; Thorsby and Ronningen, 1993). Analysis of the HLA regions is useful for tissue typing prior to tissue or organ transplantation or for identity testing in forensics or other fields. To demonstrate the usefulness of BESS to distinguish QB1 alleles, several genotypes of the HLA gene were cloned into a pUC19 plasmid vector and subjected to analysis using BESS. In this example, incorporation of a non-canonical nucleotide into DNA according to the BESS procedure was carried out using only a single primer and multiple rounds of DNA synthesis in a thermocycler. Thus, only a linear amplification of only one strand of the nucleic acid template was obtained, in a manner similar to cycle sequencing. Therefore, the BESS procedure was used to linearly amplify single-stranded copies of DQB1 genes from the plasmids. As described previously, dU was partially substituted for dT in the single-stranded amplification products. Following digestion with UNG and endonuclease IV, the products were electrophoresed in all lanes adjacent to "T" reaction products obtained from standard cycle sequencing of the same plasmids.

Primers DB130 (5'-AGGGATCCCCGCAGAGGATTTCGTGTACC-3') and GH29 (5'-GAGCTGCAGGTAGTTGTGTCTGCACAC-3') (SEQ ID NOs:3 and 4) (Bugawan and Ehrlich, 1991) were used to amplify exon 2 of the DQB1 gene from human peripheral blood DNA (Novagen, Madison, Wis.). The blood samples from five individuals were used for the DNA preparation, which should contain many alleles of the HLA gene target. Fifty microliter reactions containing 50 mM Tris-HCl pH 9.0, 20 mM ammonium sulfate, 1.5 mM magnesium chloride, 0.2 mM each of dATP, dGTP, dTTP and dCTP, 0.1 microgram each of DB130 and GH29 primers, 0.5 microgram human DNA, and 1 unit of Taq DNA polymerase (Perkin-Elmer, Branchburg, N.J.) were amplified in an MJ Research DNA Engine thermal cycler. The samples were denatured at 94° for 3 minutes, then subjected to thirty cycles of 93° for 10 seconds and 60° for 40 seconds, followed by 75° for 3 minutes. The thermal cycler was programmed to begin timing when the sample reaches the designated temperature.

The resulting 250 bp PCR product was digested with restriction endonucleases Bam HI and Pst I, which cleave the product within its primer-encoded regions. The PCR product was purified by polyacrylamide gel electrophoresis and elution from gel fragments. Plasmid pUC19 was digested with Bam HI and Pst I, treated with HK Phosphatase (Epicentre Technologies, Madison, Wis.), and ligated with the PCR product. Ampicillin-resistant colonies were screened for the presence of the PCR product in their plasmids by PCR using standard forward (5'-CGCCAGGGTTTTCCCAGTCACGAC-3') and reverse (5'-AGCGGATAACAATTTCACACAGGA-3') M13 primers (SEQ ID NOs:5 and 6). Candidate bacterial colonies were swabbed with a polypropylene pipette tip and added to PCR mixtures which were cycled as above in a DNA Engine thermal cycler. PCR products encoding HLA genes were mapped by restriction endonuclease digestion (Mitsunaga, et al., 1995) Three unique clones were selected for further analysis using BESS.

For BESS analysis, DNA synthesis was primed from the three HLA clones in a manner analogous to cycle sequencing, but with a mixture of dGTP, dCTP, dTTP, dATP and dUTP as previously described in place of a dideoxy-termination mixture. The single-stranded products of thirty cycles of linear amplification were subjected to UNG and endonuclease IV digestion in the presence of 10 mM EDTA as previously described, and were electrophoresed in a denaturing polyacrylamide gel. For comparison, the nucleotide sequences of the same three clones were determined using the SequiTherm Cycle Sequencing Kit (Epicentre Technologies, Madison, Wis.).

The BESS technique gave a unique set of bands for each HLA genotype, well correlated with the T sequencing lanes obtained by cycle sequencing each clone, except that, as expected and as in the previous examples, the BESS-derived bands migrated slightly more rapidly in the gel than the corresponding dideoxy-sequencing bands. The sequence-related data obtained using BESS was even more accurate than that obtained using standard cycle sequencing. Thus, the presence of dideoxy-sequencing artifacts in one region of the gel that were not present in the BESS products lanes aided the correct interpretation of the DNA sequence data. From this example, it is clear that the invention is not limited to sequence screening of PCR products or of double-stranded DNA molecules.

A kit may be made for determining the HLA genotype of human DNA samples using BESS. A kit containing the reagents listed below could be used in conjunction with a thermostable DNA polymerase such as Tth or Taq DNA polymerase (Perkin-Elmer Corp.) in order to perform PCR. The kit might contain: HLA-specific primers at 0.1 micrograms per microliter; a dNTP mixture containing 2.5 mM each of dGTP, dCTP and dATP, 2 mM dTTP and 0.5 mM dUTP; a DNA polymerase buffer containing 1.0 M Tris-HCl, pH 9.0, and 400 mM ammonium sulfate; 1 unit per microliter of uracil-DNA glycosylase; 50 mM EDTA; 25 mM magnesium chloride; 1 unit per microliter of *E. coli* Endonuclease IV; and a Stop Buffer containing 95% formamide, 10 mM EDTA, pH 9.5, 10 mM NaOH and 0.1% each of bromophenol blue and xylene cyanol.

The kit could be used in a similar manner to methods described in Examples 1 through 4 and FIGS. 1 through 5. Specifically, the DQB1 group of HLA genes could be amplified from human DNA obtained from peripheral blood or cheek (buccal) swabs in a 50 microliter mixture containing 50 mM Tris-HCl, pH 9.0, 20 mM ammonium sulfate, 1.5 mM magnesium chloride, 0.2 mM each of dATP, dGTP and dCTP, 0.16 mM dTTP, 0.04 mM dUTP, 0.1 micrograms each of primers DB130 and GH29 (SEQ ID NOs:3 and 4), approximately 0.5 micrograms of human DNA, and 1 unit of Taq DNA polymerase (Perkin-Elmer). The mixture could be denatured at 94° C. for three minutes, and then cycled thirty times at 93° C. for 10 seconds and 60° C. for 40 seconds and then ten minutes at 75° C. Then, after addition of EDTA to a final concentration of 10 mM, the amplification products could be cleaved by treatment with 1 unit each of uracil-DNA glycosylase and Endonuclease IV for ten minutes at room temperature. Following addition of the Stop Buffer, the samples could be denatured by incubating for five minutes at 95° C. and then analyzed by electrophoresis in an 8% polyacrylamide-8 M urea gel. The migration of the bands generated from samples using the BESS procedure could be compared to BESS reaction products from cloned DQB1 genes, perhaps included as a control in the kit, or with DNA size standards, which could also be included in the kit. The primers in the kit may be labelled by some means, preferably by a non-radioactive means, and an automated scanner and/or image analysis system could be used to compare the band patterns of samples with the controls.

REFERENCES

U.S. Patent Documents

U.S. Pat. No. 4,683,202;
U.S. Pat. No. 4,873,192;
U.S. Pat. No. 5,035,996;
U.S. Pat. No. 5,418,149.

INTERNATIONAL PATENT APPLICATIONS

WO 95/06752; Shaw and Porter; 3/1995.

OTHER PUBLICATIONS

Bessmans, et al., "Enzymatic Synthesis of Deoxyribonucleic Acid. III. The Incorporation of Pyrimidine and Purine Analogs into Deoxyribonucleic Acid", *Proc. Natl. Acad. Sci. USA* 44:633–640, 1958.

Bugawan and Ehrlich, "Rapid Typing of HLA-DQB1 DNA Polymorphism Using Nonradioactive Oligonucleotide Probes and Amplified DNA", *Immunogenetics* 33:163–170, 1991.

Cannon, et al., "5-hydroxymethyl Cytosine DNA Glycosylase Activity in Mammalian Tissue", *Biochem. Biophys. Res. Commun.* 151:1173–1179, 1988.

Cook, et al., "Enzyme-Labeled Oligonucleotides for the Detection of $Alpha_1$-Antitrypsin Deficiency: Optimization of Enzyme Activity for Single Point Mutation Detection", *Annals of Clinical Biochemistry* 32:91–93, 1995.

Cotton, "Current Methods of Mutation Detection", *Mutation Research* 285:125–144, 1993.

Cox, "$Alpha_1$-Antitrypsin Deficiency", in The Metabolic Basis of Inherited Disease, 6th Edition, Scriver, et al. eds., McGraw-Hill, New York, pp. 2409–2437, 1990.

Demple and Harrison, "Repair of Oxidative Damage to DNA", *Annual Rev. Biochemistry* 63:915–948, 1994.

Duncan, "DNA Glycosylases", (1981), in The Enzymes, Boyer ed., 14:565–586, 1981.

Fahy, et al., "Self-Sustained Sequence Replication (3SR): An Isothermal Transcription-based Amplification System Alternative to PCR", *PCR Methods and Applications* 1:25–33, 1991.

Kwoh, et al., "Transcription-based amplification system and detection of amplified human immunodeficiency virus type I with a bead-based sandwich hybridization format", *Proc. Natl. Acad. Sci. USA* 86:1173–1177, 1989.

Lindahl, "An N-Glycosylase from *Escherichia coli* That Releases Free Uracil from DNA Containing Deaminated Cytosine Residues", *Proc. Natl. Acad. Sci. USA* 71:3649–3653, 1974.

Lindahl, "DNA Glycosylases, Endonucleases for Apurinic/Apyrimidinic Sites, and Base Excision-Repair", *Progress in Nucleic Acid Research* 22:135–192, 1979.

Karran and Lindahl, "Enzymatic Excision of Free Hypoxanthine from Polydeoxy-nucleotides and DNA Containing Deoxyinosine Monophosphate Residues", *J. Biol. Chem.* 253:5877–5879, 1978.

Karran and Lindahl, "Hypoxanthine in Deoxyribonucleic Acid: Generation by Heat-Induced Hydrolysis of Adenine residues and Release in Free Form by a Deoxyribonucleic Acid Glycosylase from Calf Thymus", *Biochemistry* 19:6005–6011, 1980.

Kazazian, et al., "Prenatal Diagnosis of Sickle Cell Anemia-1988", *Annals of the New York Academy of Sciences* 565:44–47, 1989.

Kunkel, 1985, *Proc. Natl. Acad. Sci. USA* 82:488–492.

Maxam and Gilbert, "A New Method for Sequencing DNA", *Proc. Natl. Acad. Sci. USA* 74:560–564, 1977.

Merajver, et al., "Somatic Mutations in the BRCA1 Gene in Sporadic Ovarian Tumors", *Nature Genetics* 9:439–443, 1995.

Mitsunaga, et al., "High Resolution HLA-DQB1 Typing by Combination of Group-Specific Amplification and Restriction Fragment Length Polymorphism", *Human Immunology* 42:307–314, 1995.

Myers and Gelfand, "Reverse Transcription and DNA Amplification by a *Thermus thermophilus* DNA Polymerase", *Biochemistry* 30:7661–7666, 1991.

Nisson, et al., "Rapid and Efficient Cloning of Alu-PCR Products Using Uracil DNA Glycosylase", PCR Methods and Applications", 1:120–123, 1991.

Sagher and Strauss, "Abasic Sites From Cytosine as Termination Signals for DNA Synthesis", *Nucl. Acids Res.* 13(12):4285–4298, 1985.

Sanger, et al., "DNA Sequencing with chain-terminating inhibitors", *Proc. Natl. Acad. Sci. USA* 74:5463–5468, 1977.

Stahl and Chamberlin, "Groups on the Outside of the DNA Helix Effect Promoter Utilization by T7 RNA Polymerase", in RNA Polymerase, Losich and Chamberlin eds., Cold Spring Harbor Press, Cold Spring Harbor, N.Y., pp. 429–440, 1976.

Thorsby and Ronningen, "Particular HLA-DQ Molecules Play a Dominant Role in Determining Susceptibility to Resistance to Type 1 (Insulin-Dependent) Diabetes Mellitus", *Diabetologia* 36:371–377, 1993.

Walker, "Strand Displacement Amplification", In: Novel Amplification Technologies for DNA/RNA-Based Diagnostics, a book presented at a meeting of the same name on Apr. 20–22, 1994 in San Francisco, Calif., organized by International Business Communications, 225 Turnpike Road, Southborough, Mass., 1772–1749.

Warner, et al., 1979, *J. Biol. Chem.* 245(16):4734–7539.

Yap and McGee, "Detection of Mutations by PCR", in PCR Technology, Griffin and Griffin, eds., CRC Press, Boca Raton, Fla., pp. 107–120, 1994.

We claim:

1. A method for characterizing a nucleic acid molecule comprising:
   a) synthesizing DNA in the presence of a reaction mixture comprising:
      (i) a nucleic acid template,
      (ii) a primer molecule that contains a nucleotide sequence at least part of which is sufficiently complementary to a portion of the template to hybridize therewith,
      (iii) an enzyme that extends the primer so that a DNA molecule may be synthesized,
      (iv) four canonical deoxynucleoside triphosphates, and
      (v) at least one non-canonical deoxynucleoside triphosphate, wherein the non-canonical deoxynucleoside triphosphate is one that is incorporated with fidelity into the synthesized DNA in place of only one canonical deoxynucleoside triphosphate;
   b) contacting the synthesized DNA with an N-glycosylase that excises a base portion of the non-canonical deoxynucleoside triphosphate from said synthesized DNA, whereby an abasic site is created;
   c) treating the DNA in such manner that said treatment results in breakage of a phosphodiester backbone at all abasic sites, whereby at least two DNA fragments are created; and
   d) separating the fragments according to size.

2. The method of claim 1 wherein the fragments are detected by transferring said size-separated fragments to a solid support and then revealing the presence of said fragments by hybridization thereto of a labelled complementary probe.

3. The method of claim 1 wherein the synthesized DNA is labelled with a detectable probe.

4. The method of claim 1 wherein the template is a DNA molecule and the enzyme of step (a) is a DNA-dependent DNA polymerase.

5. The method of claim 4 wherein the enzyme is thermostable.

6. The method of claim 1 wherein the template is an RNA molecule and the enzyme of step (a) is an RNA-dependent DNA polymerase.

7. The method of claim 6 wherein the enzyme is thermostable.

8. The method of claim 1 wherein the non-canonical deoxynucleoside triphosphate is 2'-deoxyuridine-5'-triphosphate and the N-glycosylase is uracil-N-glycosylase.

9. The method of claim 1 wherein the non-canonical deoxynucleoside triphosphate is 2'-deoxyinosine-5'-triphosphate and the N-glycosylase is hypoxanthine-N-glycosylase.

10. The method of claim 1 wherein a non-canonical base is modified after incorporation into the synthesized DNA by treating the synthesized DNA in order to make the modified base a non-canonical base which is susceptible to loss upon treatment of the synthesized DNA with an N-glycosylase.

11. The method of claim 1 additionally comprising the step of providing three additional DNA synthesis reactions, to provide a total of four DNA synthesis reactions, wherein a different non-canonical deoxynucleoside triphosphate is used in each reaction.

12. A method for determining the complete nucleotide sequence of a nucleic acid template by analyzing the nucleic acid fragments of claim 11.

13. The method of claim 1 wherein step (c) comprises heating the DNA to break the phosphodiester backbone at all abasic sites.

14. The method of claim 1 wherein step (c) comprises using a basic solution to effect the breakage of the phosphodiester backbone at all abasic sites.

15. The method of claim 1 wherein step (c) comprises using an enzyme to effect the breakage of the phosphodiester backbone at all abasic sites.

16. The method of claim 15 wherein step (c) comprises using an AP endonuclease to effect the breakage of the phosphodiester backbone at all abasic sites.

17. The method of claim 1 additionally comprising the step of providing at least two different non-canonical nucleotides in the synthesizing step, wherein the reaction is divided into separate aliquots in the contacting step so that a different N-glycosylase is provided for each aliquot.

18. The method of claim 1 wherein DNA synthesis is a part of a method for amplification of the template nucleic acid.

19. The method of claim 1 wherein DNA synthesis is a part of amplification of a template nucleic acid using the Polymerase Chain Reaction.

20. The method of claim 1 wherein DNA synthesis is a part of a NASBA reaction.

21. The method of claim 1 wherein DNA synthesis is a part of 3SR.

22. The method of claim 1 wherein DNA synthesis is a part of Strand Displacement Amplification.

23. The method of claim 1 in which electrophoresis is used to separate the DNA fragments.

24. A kit for characterizing a nucleic acid template, comprising:

an enzyme capable of extending a primer bound to a nucleic acid template so that a DNA molecule may be synthesized, four canonical deoxynucleoside triphosphates, at least one non-canonical deoxynucleoside triphosphate, wherein the non-canonical deoxynucleoside triphosphate is one that is incorporated with fidelity into the synthesized DNA in place of only one canonical deoxynucleoside triphosphate; an N-glycosylase capable of excising the base portion of each respective non-canonical deoxynucleoside triphosphate from said synthesized DNA, and an AP endonuclease.

25. The kit of claim 24 additionally comprising at least one primer molecule.

* * * * *